United States Patent
Hagar (10) Patent No.: US 10,497,467 B2
(45) Date of Patent: Dec. 3, 2019

(54) SYSTEMS AND METHODS FOR OPTIMIZING DIAGNOSTICS AND THERAPEUTICS WITH METABOLIC PROFILING

(71) Applicant: Amit Hagar, Bloomington, IN (US)

(72) Inventor: Amit Hagar, Bloomington, IN (US)

(73) Assignee: Cellsor LLC, Bloomington, IN (US)

( * ) Notice: Subject to any disclaimer, the term of this patent is extended or adjusted under 35 U.S.C. 154(b) by 0 days.

(21) Appl. No.: 16/091,973

(22) PCT Filed: Feb. 17, 2017

(86) PCT No.: PCT/US2017/018530
§ 371 (c)(1),
(2) Date: Oct. 5, 2018

(87) PCT Pub. No.: WO2018/151732
PCT Pub. Date: Aug. 23, 2018

(65) Prior Publication Data
US 2019/0180849 A1 Jun. 13, 2019

(51) Int. Cl.
| | |
|---|---|
| *G01N 33/48* | (2006.01) |
| *G01N 33/50* | (2006.01) |
| *G16C 20/70* | (2019.01) |
| *G16H 50/20* | (2018.01) |
| *G16H 20/30* | (2018.01) |
| *A61B 5/02* | (2006.01) |
| *A61B 5/145* | (2006.01) |
| *A61B 5/22* | (2006.01) |

(Continued)

(52) U.S. Cl.
CPC ............... *G16C 20/70* (2019.02); *A61B 5/02* (2013.01); *A61B 5/14532* (2013.01); *A61B 5/14542* (2013.01); *A61B 5/14546* (2013.01); *A61B 5/222* (2013.01); *A61B 5/4842* (2013.01); *A61B 5/4866* (2013.01); *A61B 5/4884* (2013.01); *A61B 5/7275* (2013.01); *A63B 24/0075* (2013.01); *G16H 20/30* (2018.01); *G16H 50/20* (2018.01); *G16Z 99/00* (2019.02)

(58) Field of Classification Search
None
See application file for complete search history.

(56) References Cited

U.S. PATENT DOCUMENTS

| | | | |
|---|---|---|---|
| 7,343,197 B2 | 3/2008 | Shusterman | |
| 2013/0225477 A1* | 8/2013 | Varadhachary | A61K 38/40 514/1.4 |
| 2014/0214446 A1* | 7/2014 | Nusbaum | G09B 19/00 705/2 |

FOREIGN PATENT DOCUMENTS

| | | |
|---|---|---|
| WO | 0078208 A1 | 12/2000 |
| WO | 2015042476 A1 | 3/2015 |

OTHER PUBLICATIONS

Jones et al., Exercise-oncology research: Past, present and future, Dec. 17, 2012, pp. 195-215, vol. 52, Acta Oncologica, Durham, North Carolina, USA.

(Continued)

*Primary Examiner* — Russell S Negin
(74) *Attorney, Agent, or Firm* — D'Hue Law LLC; Cedric A. D'Hue (57) ABSTRACT

The present disclosure is directed towards methods for calculating disease progression rates and sojourn times of solid tumors from metabolic markers and using this calculation to optimize patient-specific diagnosis, scheduling of screening procedures, and dosage or frequency of treatment.

8 Claims, 6 Drawing Sheets

(51) Int. Cl.
  *A61B 5/00*   (2006.01)
  *A63B 24/00*  (2006.01)
  *G16Z 99/00*  (2019.01)

(56) References Cited

OTHER PUBLICATIONS

USPTO, International Preliminary Report on Patentability, in related application PCT/US17/18530, dated Oct. 25, 2018, 6 pages.

Betof et al., Effects and potential mechanisms of exercise training on cancer progression, May 17, 2012, pp. 575-587, vol. 30, Brian, Behavior and Immunity, available at https://www.sciencedirect.com/science/article/pii/S0889159112001080.

Foley et al., Fatty Acids and Exercise Affect Glucose Transport but not Tumour Growth in F-344 Rats, 2004, pp. 604-622, vol. 29, issue 5, Can. J. Appl. Physiol., available at http://www.nrcresearchpress.com/doi/abs/10.1139/h04-039.

USPTO, International Search Report, in related application PCT/USI7/18530, dated May 15, 2017, 3 pages.

USPTO, Written Opinion of the International Search Authority, in related application PCT/US17/18530, dated May 15, 2017, 5 pages.

USPTO, Article 34 amendment, in related application PCT/US17/18530, dated May 15, 2017, 5 pages.

Hagar, Amit, Endurance Exercise and Solid Tumor Progression, Second Annual Indiana University Bloomington Innovation Conference, Mar. 31, 2016, Bloomington, Indiana.

Indiana University, Research, Industry come together during the second annual Indiana University Bloomington Innovation Conference, Apr. 4, 2016, Bloomington, Indiana.

Indiana University, Five Indiana University Bloomington professors win grants from new translational research program, Jun. 1, 2015, Bloomington, Indiana.

\* cited by examiner

FIG. 1

Figure 2:
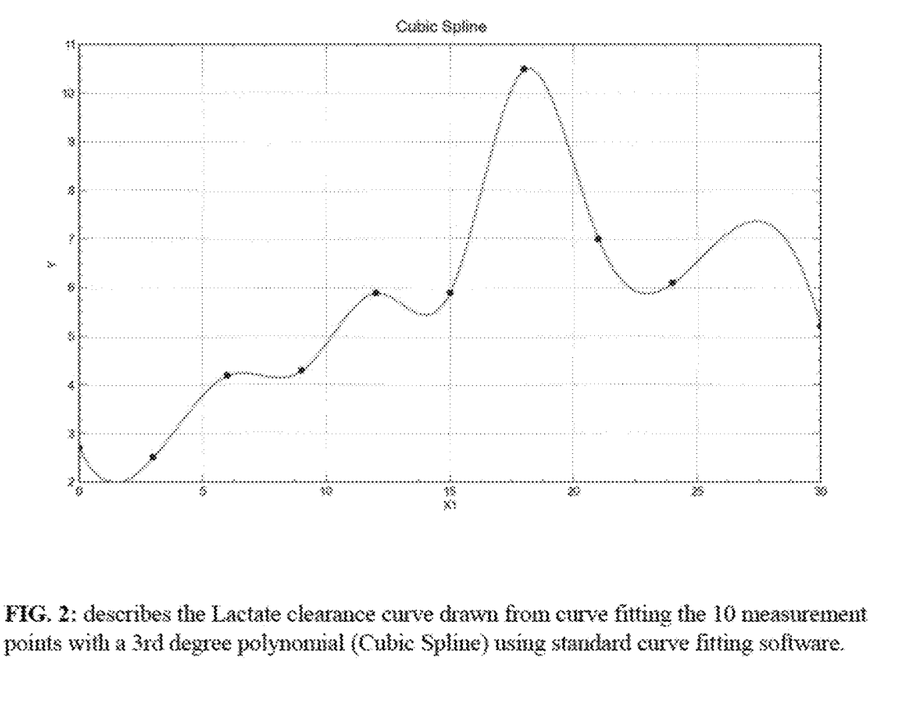
FIG. 2 describes the Lactate clearance curve drawn from curve fitting the 10 measurement points with a $3^{rd}$ degree polynomial (Cubic Spline) using standard curve fitting software.

FIG. 2: describes the Lactate clearance curve drawn from curve fitting the 10 measurement points with a 3rd degree polynomial (Cubic Spline) using standard curve fitting software.

Figure 3:
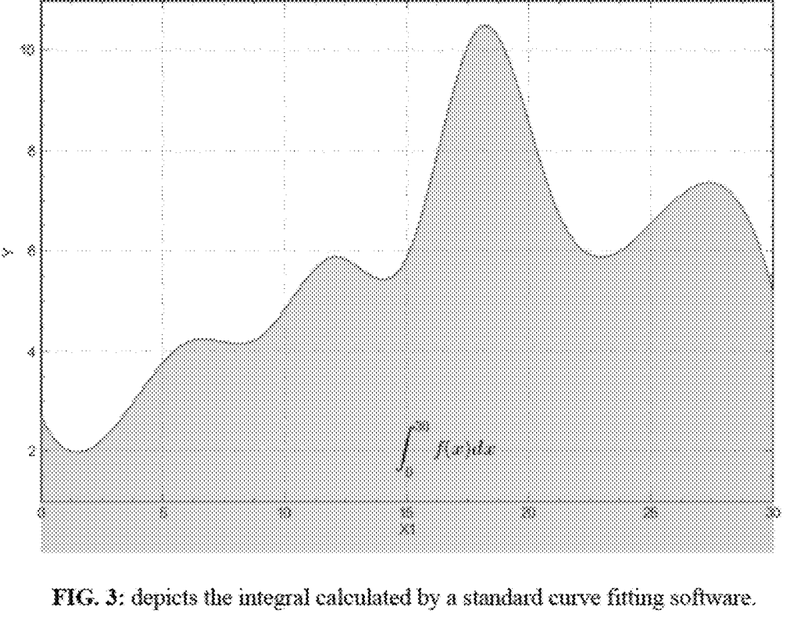
FIG. 3. depicts the integral calculated by a standard curve fitting software.

FIG. 3: depicts the integral calculated by a standard curve fitting software.

|     | yrs | lb  | in  | /(h2)*703 | Hg  | H_Rest | 208.5-0.7*age |
| --- | --- | --- | --- | --- | --- | --- | --- |
| Age | 78  |     |     |     |     |     |     |
|     |     | Wg  |     |     |     |     |     |
|     |     | 159 |     |     |     |     |     |
|     |     |     | Hg  |     |     |     |     |
|     |     |     | 65  |     |     |     |     |
|     |     |     |     | BMI |     |     |     |
|     |     |     |     | 26.5 |     |     |     |
|     |     |     |     |     |     | 74  |     |
|     |     |     |     |     |     |     | H_Max |
|     |     |     |     |     |     |     | 154 |
| 41  |     |     |     |     |     |     |     |
| MP  |     |     |     |     |     |     |     |

BMI=w/(h^2)*703
HR = (220-age-HRrest)*%+HRrest
HRmax = 208.5-0.7*age

|     | 0   | 3m  | 6m  | 9m  | 12m | 15m | 18m | 21m | 24m | 30m |
| --- | --- | --- | --- | --- | --- | --- | --- | --- | --- | --- |
|     |     | 50% | 55% | 60% | 65% | 70% | Rest | Rest | Rest | Rest |
|     | La0 | La1 | La2 | La3 | La4 | La5 | La6 | La7 | La8 | La9 |
|     | 1.4 | 2.1 | 2.6 | 3.3 | 3.9 | 3.8 | 3.4 | 3.2 | 2.3 | 2.0 |
| HR  |     | 108 | 111 | 115 | 118 | 122 |     |     |     |     |
| W   |     | 34  | 39  | 39  | 46  | 46  |     |     |     |     |

|              |       |       |       |       |       |
| ---          | ---   | ---   | ---   | ---   | ---   |
| Area         | 5.37  | 7.03  | 8.80  | 10.92 | 11.71 |
| W-Weighted   | 15.79 | 18.03 | 22.56 | 23.74 | 25.46 |

| Exercise  | 105.58 |
| --- | --- |
| Clearance | 39.28  |
| LAC       | 144.86 |

| score | age cor. |
| --- | --- |
| 144.9 | 171.66 |

FIG. 4

$$[DT] = 10^{\wedge}(a-b*\log_{10}[MET])$$

where the range of these parameters for a 95% confidence level (in this particular embodiment for Invasive Ductal Carcinoma) is:

$$a = 3.53 \pm 0.11 \quad \text{and} \quad b = 4.71 \pm 0.41$$

SYSTEMS AND METHODS FOR OPTIMIZING DIAGNOSTICS AND THERAPEUTICS WITH METABOLIC PROFILING

This application is a 371 national stage application of international PCT application number PCT/US17/18530, filed Feb. 17, 2017, the subject matter of which is expressly incorporated by reference.

FIELD OF THE DISCLOSURE

This disclosure relates to personalized medicine. More specifically, this disclosure relates to a method for optimizing diagnostics and therapeutics of solid tumors with patient specific disease progression rates and sojourn times using metabolic profiling in an exercising setup.

BACKGROUND

Current decision-making processes on scheduling of diagnostic and screening procedures, or dosage and frequency regimes for therapeutic procedures for Breast, Colon, Prostate, lung, and other solid tumors, are based on epidemiological data for patient categories discriminated by age, genetic risk, family history, and few personal clinical features which may limit the sensitivity of the screening apparatus, or the efficacy of the respective treatment.

One unknown in these decision-making processes is the patient-specific sojourn time of the disease in the phase to which the diagnostic or therapeutic procedure is intended to apply. The sojourn time is a function of the progression rate of the disease, and many of these procedures are optimal and most effective when synchronized with this rate. Lack of appropriate methods to predict progression rates for individual patients is the reason why sojourn times remain unknown. As a result, patients are often treated with "one size fits all" strategy, in which the sojourn times are calculated via statistical averages from the population. The best example for this strategy is the recent recommendation from the US Preventive Service Task Force that all women between 50 and 74 should go through bi-ennial mammogram screening. This recommendation may be optimal to some women, but will fail to early-detect those with fast progression rate, and will lead to unnecessary stress and excess radiation in those with slow progression rate.

Since the progression rates of solid tumors vary considerably between diagnosed patients, additional discriminatory measurements would have profound prognostic, diagnostic and therapeutic value, particularly for personalized medicine, and will ultimately lead to more informative diagnoses and more effective treatments and prognostics.

Contrary to global measures like BMI, which is mostly non-indicative for personalized medicine, the intracellular metabolic balance between oxidative phosphorylation, or OXPHOS (the production of ATP in the mitochondria by burning Pyruvate with Oxygen) and Glycolysis (the production of ATP in the cytosol by the breakdown of Pyruvate to Lactate without Oxygen) strongly affects disease progression rates, directly through biosynthesis and indirectly through enhancement of immune response, and thus provides a valuable personal diagnostic and therapeutic discriminant for the above decision-making processes. A possible context where this balance can become evident and measurable is aerobic exercise, where energy from aerobic and non-aerobic metabolism is concurrently produced in the skeletal muscles, yet while athletes use some metabolic markers during aerobic exercise to customize their training zones, so far there is no attempt to measure the intracellular metabolic balance between OXPHOS and Glycolysis in vivo in humans. Current research in animal models does involve measurement of this metabolic balance, but is directed solely at drug discovery, and not at predicting patient-specific progression rates and sojourn times in animals or in humans.

Thus, there remains a considerable need for methods that can conveniently predict patient-specific disease progression rates and sojourn times with metabolic markers, so that they can be incorporated into the current decision-making processes on prognostics, diagnostics and therapeutics of solid tumors.

SUMMARY

Embodiments herein concerns methods for optimizing diagnostics, and therapeutic procedures in a human patient, comprising the steps of measuring the level of at least one metabolic marker in a patient, and calculating disease progression rates and sojourn times, predicting at least one incident selected from the group consisting of: diagnosis, timing of screening procedures, a type of treatment, a dosage of treatment, and a frequency of treatment.

In some embodiments, methods for optimizing diagnostics, and therapeutic procedures may include further the steps of providing the patient with an exercising equipment, allowing the patient to exercise on the exercising equipment for a period of time. Some embodiments may further include the step of adjusting an exercise level of the patient to the patient's age and heart rate and/or the step of entering the measurement of the at least one metabolic marker to an algorithm.

In accordance with these embodiments, certain metabolic markers may include, but not limited to, glucose, lactate, and pyruvate. In some embodiments, a patient may be fasted for at least 8 hour.

BRIEF DESCRIPTION OF THE DRAWINGS

The above mentioned and other features and objects of this disclosure, and the manner of attaining them, will become more apparent and the disclosure itself will be better understood by reference to the following description of exemplary embodiments of the disclosure taken in conjunction with the accompanying drawings, wherein.

Corresponding reference characters indicate corresponding parts throughout the several views. Although the drawings represent embodiments of the present disclosure, the drawings are not necessarily to scale and certain features may be exaggerated in order to better illustrate and explain the present disclosure. The exemplification set out herein illustrates exemplary embodiments of the disclosure, in various forms, and such exemplifications are not to be construed as limiting the scope of the disclosure in any manner.

DETAILED DESCRIPTION

The embodiment disclosed below is not intended to be exhaustive or limit the disclosure to the precise form disclosed in the following detailed description. Rather, the embodiments are chosen and described so that others skilled in the art may utilize its teachings.

One of ordinary skill in the art will realize that the embodiments provided can be implemented in hardware, software, firmware, and/or a combination thereof. Programming code according to the embodiments can be implemented in any viable programming language such as C, C++, HTML, XTML, JAVA or any other viable high-level programming language, or a combination of a high-level programming language and a lower level programming language.

As used herein, the modifier "about" used in connection with a quantity is inclusive of the stated value and has the meaning dictated by the context (for example, it includes at least the degree of error associated with the measurement of the particular quantity). When used in the context of a range, the modifier "about" should also be considered as disclosing the range defined by the absolute values of the two endpoints. For example, the range "from about 2 to about 4" also discloses the range "from 2 to 4."

Where a range of values is provided, it is understood that each intervening value, to the tenth of the unit of the lower limit unless the context clearly dictates otherwise, between the upper and lower limit of that range and any other stated or intervening value in that stated range is encompassed within the present disclosure. The upper and lower limits of these smaller ranges may independently be included in the smaller ranges is also encompassed within the present disclosure, subject to any specifically excluded limit in the stated range. Where the stated range includes one or both of the limits, ranges excluding either or both of those included limits are also included in the present disclosure.

Unless defined otherwise, all technical and scientific terms used herein have the same meaning as commonly understood by one of ordinary skill in the art to which the present disclosure belongs. Although any methods and materials similar or equivalent to those described herein can also be used in the practice or testing of the present disclosure, a limited number of the exemplary methods and materials are described herein.

It must be noted that as used herein and in the appended claims, the singular forms "a", "an", and "the" include plural referents unless the context clearly dictates otherwise.

A therapeutically effective amount is an amount of a biologically active compound that has a single or cumulative beneficial effect on the health or well being of a patient.

The concept of measuring intracellular metabolic markers in humans during exercise and, based on a functional relation between these markers and sojourn times of solid tumors, using these markers to calculate disease progression rates and sojourn times to optimize diagnostics and therapeutic procedures, customizing these procedures to the individual patient.

Embodiments include a method for measuring metabolic markers in humans and calculating progression rates and sojourn times therefrom, comprising: (a) a measurement set up of (i) a reclined bike or a treadmill; (ii) Lactate and Glucose Analyzers; (iii) a human subject fasting at least 8 hrs; (b) a measurement protocol comprising the steps of: (i) 15 minutes of incremental aerobic exercise, adjusted to the subject's age and Heart Rate at rest and calculated via Karvonen formula [(220−age−HRrest)*P %+HRrest], from P=50% through P=55%, P=60%, P=65% and up to P=70% of personal Maximal Heart Rate, spending 3 minutes in each Heart Rate level, followed by 15 minutes of rest; (ii) measurements of Lactate serum concentration at Minute 0, 3, 6, 9, 12, 15, 18, 21, 24, and 30; and (iii) measurements of average power output in Watt at Minute 3, 6, 9, 12, and 15; (c) three algorithms.

Some embodiments may include a computer interface that allows entering the results from the measurement protocol (b) as input to the algorithms from (c).

Some embodiments may include an algorithm from step (c) that takes as an input the patient's age and the measurements in protocol (b)(ii-iii) and gives as an output the patient's metabolic score.

Some embodiments may include an algorithm that takes as input the metabolic score above and gives as an output the personal progression rate of the disease (doubling time in days).

Some embodiments may include an Algorithm that takes as an input the personal progression rate above and yields as an output the sojourn time of the disease between two designated time points of a particular clinical procedure, so that a schedule for a diagnostic procedure, or a dosage and a frequency for a therapeutic procedure, can be calculated based on this sojourn time In a preferred embodiment of the present disclosure, the measurement setup described above involves a human subject who can independently perform the measurement protocol described above, either at home or at the physician office, and subsequently receive recommendation for personal scheduling, dosage, or frequency of diagnostic or therapeutic procedures, based on the personal sojourn time calculated from the subject's metabolic score.

The present disclosure is designed so that the three algorithms that can be implemented with data from the measurement protocol (b) either by using the computer interface or by incorporating these algorithms as hardware into one or more components of the measurement setup in (a)(i-ii), so that the data from the setup will be automatically fed into the concatenated chain of algorithms at the end of the protocol.

Various objects, features, aspects, and advantages of the present disclosure will become more apparent from the following detailed description of preferred embodiments of the present disclosure, along with the accompanying drawings in which like numerals represent like components.

Figure 1:
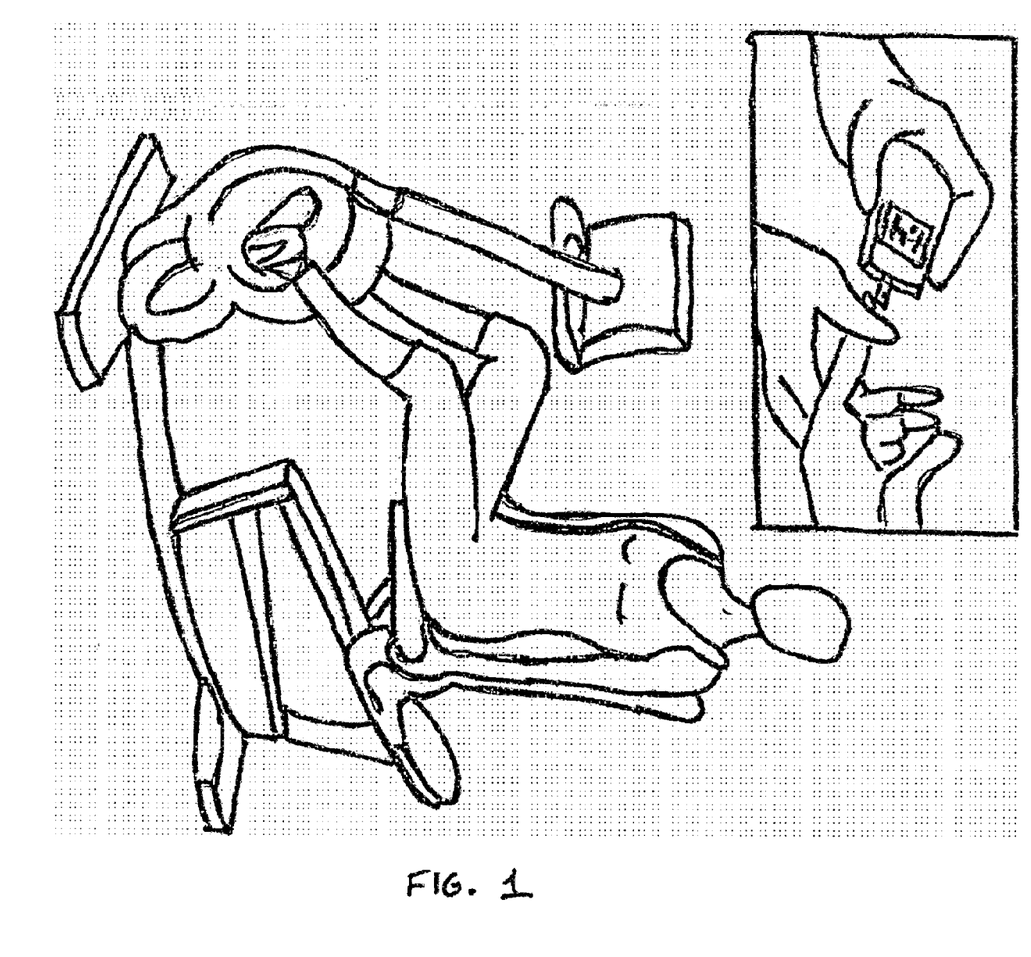
FIG. 1 represents a possible embodiment of two components of the measurement setup.

FIG. 1 represents a possible embodiment of two components of the measurement setup ((a) and (b)).

FIG. 2 describes the Lactate clearance curve drawn from curve fitting the 10 measurement points with a $3^{rd}$ degree polynomial (Cubic Spline) using standard commercial curve fitting software from. The data points are those obtained from using the apparatus in FIG. 1 on the human subject who follows the measurement protocol (b).

FIG. 3 depicts the integral calculated by the Algorithm on that curve (the area below it) between point 0 (the initial time point of the measurement protocol (b)) and point 30 (the final time point of the measurement protocol in (b)).

Figure 4:
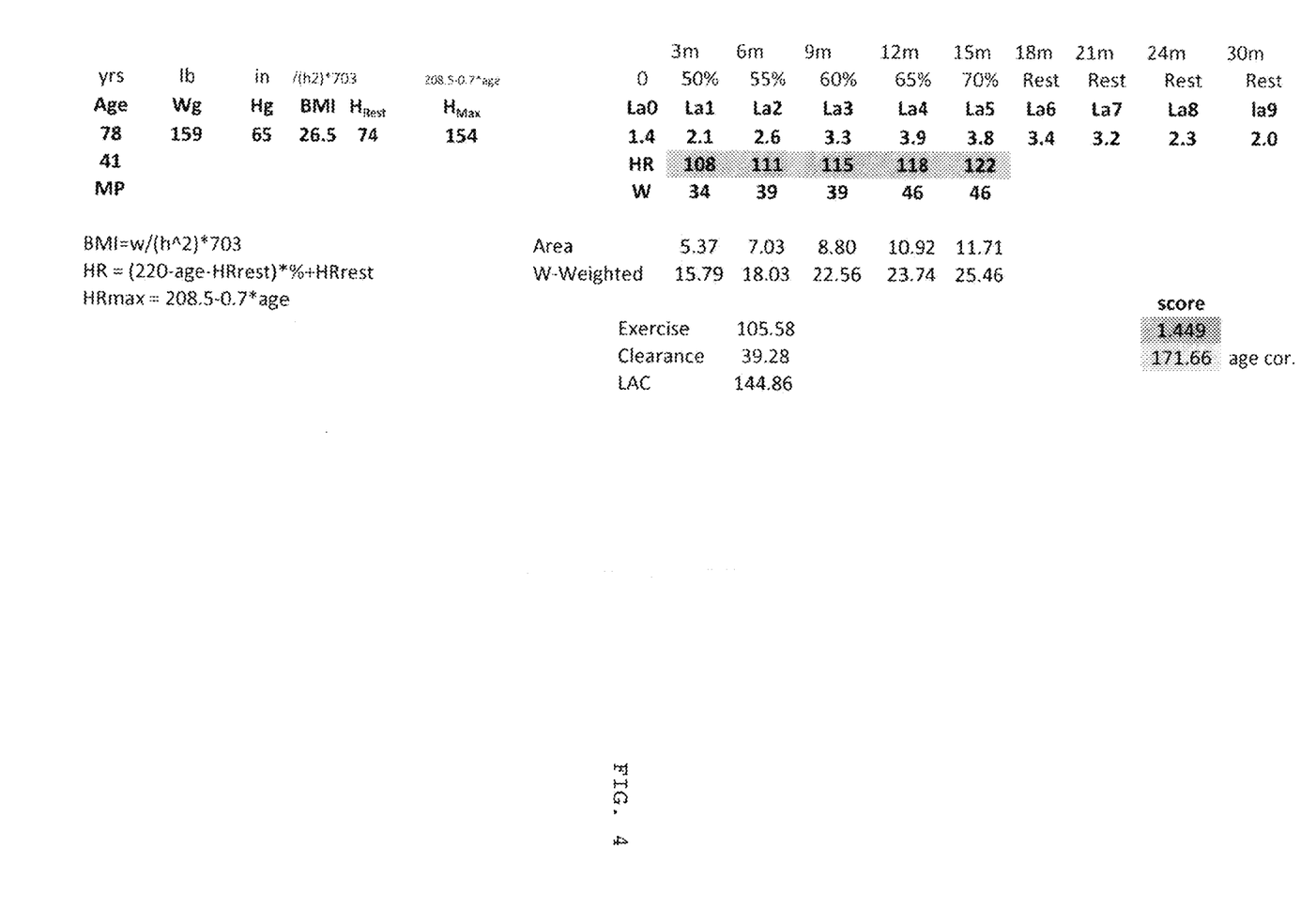
FIG. 4 depicts a possible embodiment of the computer interface allowing the user to input the data from the measurement protocol (b) into the $1^{st}$ algorithm in (c) that calculates the patient's metabolic score [MET]

FIG. 4 depicts a possible embodiment of the computer interface allowing the user to input the data from the measurement protocol (b) into the first algorithm. This algorithm works as follows:

Algorithm I:

Step 1: Calculate the integral on the Lactate clearance curve (FIG. 6) in each 3 minutes interval between 0 and 15, and divide it by W/100, where W is the average Watt output, read from the apparatus in FIG. 1 during each 3-minute segment, in 10 seconds intervals.

Step 2: Sum the 5 normalized area segments in Step 1.

Step 3: Calculate the integral on the Lactate clearance curve in the interval between minute 15 and 30.

Step 4: Sum results from Step 2 and Step 3. This is the total normalized area [LAC]

Step 5: Calculate the age correction factor [Age] by subtracting 50 from the human subject current age. [Age] can be negative.

Step 6: Multiply result from Step 5 with $$([Age]/100+1)/100$$

Step 7: Given the range of Lactate serum concentration in humans and the nature of the measurement protocol (b), the final result is a positive number between 0 and 3, designating the subject's metabolic score [MET].

Figure 5:
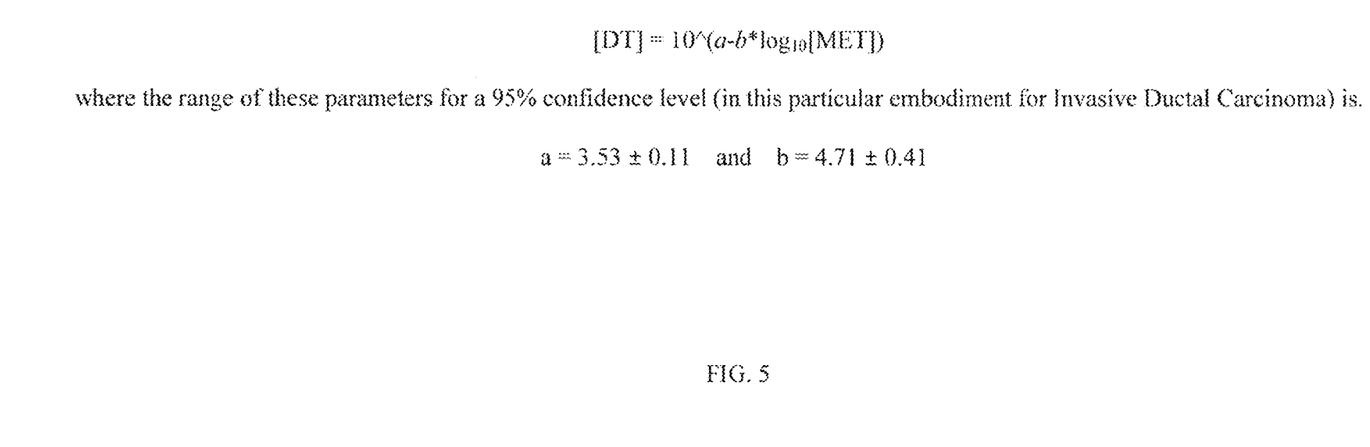
FIG. 5 depicts the $2^{nd}$ algorithm in (c) for calculating the predicted growth rate (the doubling time, measured in days, [DT]) from the patient's metabolic score [MET]

FIG. 5 depicts the algorithm for calculating the predicted growth rate (the doubling time [DT], measured in days) from the subject's metabolic score [MET]. The algorithm works as follows:

Algorithm II:

Step 1: Calculate the doubling time [DT] from the metabolic score [MET] given by Algorithm I (Step 7) using the formula:

$$[DT]=10^{\wedge}(a-b*\log_{10}[MET])$$

where the range of these parameters for a 95% confidence level (in this particular embodiment for Invasive Ductal Carcinoma) is.

$$a=3.53\pm0.11 \text{ and } b=4.71\pm0.41$$

Figure 6:
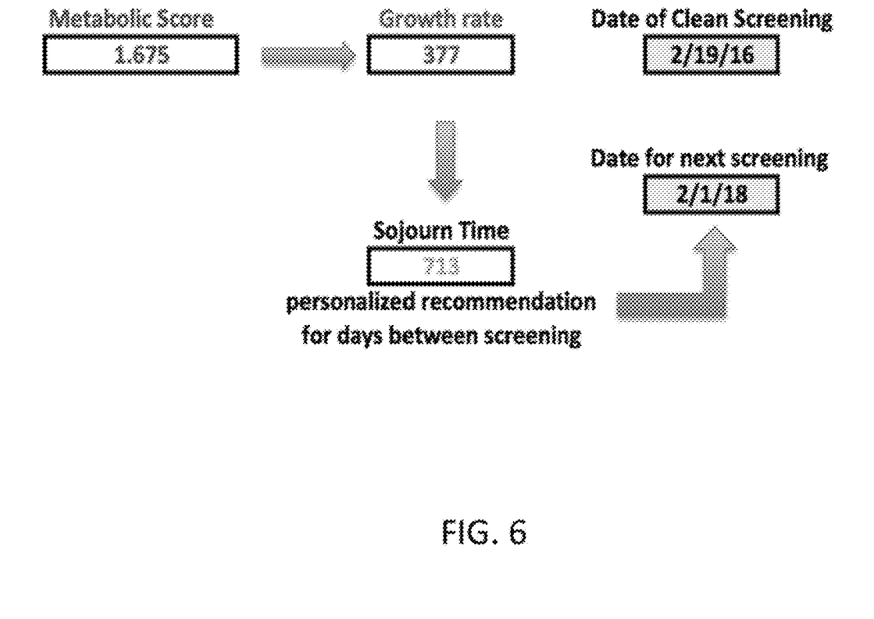
FIG. 6 depicts a possible embodiment of the computer interface for the $3^{rd}$ algorithm in (c) that computes the sojourn time [DAYS] and the receptive optimized frequency for a diagnostic procedure for a given [DT].

FIG. 6 depicts a possible embodiment of the computer interface for the algorithm that computes the sojourn time for a given [DT]. In the example presented here, a subject whose screening result is normal at a given date can use the predicted progression rate [DT] to calculate the sojourn time of the disease under the assumption that the disease exists but the screening apparatus failed to detect it because it is below or at the detection threshold. With this sojourn time the next schedule for screening can be decided using the following steps:

Algorithm III:

Step 1: Calculate sojourn time [DAYS] with $$[DAYS]=[DT]*(([RFN]*LOG_2([FN]/[T])+[RTN]*LOG_2([TN]))$$

Here [T] represents the threshold of detection of the screening apparatus in $mm^3$, ([T]=8 for digital mammography of breast tumor) and the adjustable nominators in the $LOG_2$ ([FN] and [TN]) represent a target volume of the tumor in $mm^3$ deemed appropriate for diagnostic purposes (in the embodiment in FIG. 6, [FN]=9 for the false negative case and [TN]=1 for the true negative case).

Thus the first part of the sum in each sojourn time ("([RFN]*$LOG_2$([FN]/[T])") is calculated under the assumption that the current normal mammogram is false negative and the tumor is at most at detection threshold, and the second part of the sum in each sojourn time ("([RTN]*$LOG_2$([TN))") is calculated under the assumption that the current normal mammogram is true negative but the tumor is below detection threshold, at 1 $mm^3$.

The normalizing adjustable factors 0<[RFN]<1 and [RTN]=1-[RFN] represent the statistical rate of false and true negatives of the screening apparatus, respectively (in the case of digital mammography for this particular embodiment, and according to the National Cancer Institute, [RFN] ranges between 10% and 20%).

The parameters [T] [FN] [TN] in Steps (1) of Algorithm III can be adjusted according to the specific disease, the sensitivity of the screening apparatus for that disease, and the risk-aversion of the patient.

Step 2: use [DAYS] to decide the optimal next screening date, now based on the personal sojourn time and the sensitivity of the screening apparatus, according to the following table (based on [RFN], [RTN], [FN], [TN] in the case of invasive ductal carcinoma):

If [DAYS]>730, next screening date is in 2 years
If [DAYS]<200 days, next screening date is in 6 months
If 200<[DAYS]<730, the next screening date is [DAYS] days from current date Since [DT] is calculated using the personalized metabolic score [MET], the scheduling interval may differ from the average "one size fits all" recommendation. Embodiments ensure it will be customized to the individual patient. This possible embodiment thus shows how this disclosure allows the physician and the subject to replace the prevailing decision making process on scheduling of screening which is based on an "average" sojourn time in the population with a personalized decision making process which is customized to the individual subject. The benefit of this customized process is that subjects whose sojourn time is shorter than the average could now decide to schedule their screening frequency accordingly and would have a higher probability to early detect the disease upon onset, while subjects whose sojourn time is longer than the average could now decide to avoid unnecessary stress and excess radiation by scheduling their screening less frequently.

The reduction to practice of the disclosure to other types of solid tumors may require changes in the parameters (a,b) of Algorithm II, due to known differences in cell growth in different tissues. The parameters [T] [FN] [TN] in Algorithm III will vary with the detection thresholds and the false negative rates of the respective screening modality in each disease, all this without changing any of the Independent or Dependent Claims.

Thus, specific compositions and methods of optimizing diagnostics and therapeutic schedules with metabolic profiling have been disclosed. It should be apparent, however, to those skilled in the art that many more modifications besides those already described are possible without departing from the inventive concepts herein. The inventive subject matter, therefore, is not to be restricted except in the spirit of the disclosure. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains.

Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements. The scope is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B or C may be present in a single embodiment; for example, A and B, A and C, B and C, or A and B and C.

In the detailed description herein, references to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art with the benefit of the present disclosure to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. § 112(f), unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A method for optimizing diagnostic and therapeutic procedures for solid tumors in a human patient by measuring metabolic markers during exercise, the method comprising the steps of:

providing the patient with an exercising equipment;
allowing the patient to exercise on the exercising equipment for a period of time in accordance with a measurement protocol; wherein;
adjusting an exercise level of the patient to the patient's age and heart rate;
measuring the level of at least one metabolic marker in the patient during exercise; wherein an algorithm is used to predict the personal progression rate and sojourn time from the patient's metabolic score; wherein the metabolic score is a range of Lactate serum concentration as modified by the measurement protocol;
calculating disease progression rates and sojourn times based on a personalized functional relation between the at least one metabolic marker and disease progression rates and sojourn time;
exposing a diagnostic trait of the patient;
predicting at least one incident selected from the group consisting of: timing of screening procedures, a type of treatment, a dosage of treatment, a timing of treatment, and a frequency of treatment; and
optimizing a treatment schedule relative to an average treatment schedule, wherein the treatment schedule is extended relative to the average treatment schedule when the sojourn time exceeds a first threshold value, wherein the treatment schedule is adjusted relative to the average treatment schedule when the sojourn time is between a second threshold value and the first threshold value.

2. The method of claim 1, further comprising the step of: entering the measurement of the at least one metabolic marker to an algorithm, wherein the algorithm is used to calculate a patient's metabolic score from the at least one metabolic marker; wherein an algorithm is used to predict the personal progression rate and sojourn time from the patient's metabolic score; and wherein an algorithm is used to calculate the optimal frequency of a diagnostic procedure or the optimal dosage and frequency of a therapeutic procedure from the personal progression rate and sojourn time.

3. The method of claim 1, wherein the at least one metabolic marker comprises glucose, lactate, or pyruvate.

4. The method of claim 1, wherein an algorithm is used to calculate the patient's metabolic score from the at least one metabolic marker.

5. The method of claim 1, wherein an algorithm is used to predict diagnostic procedures of the patient.

6. The method of claim 1, wherein the measurement protocol comprises the steps of:
(i) performing 15 minutes of incremental aerobic exercise;
(ii) adjusting the 15 minutes of incremental aerobic exercise to the subject's age and Heart Rate at rest and calculated via Karvonen formula; and
(iii) spending 3 minutes in each Heart Rate level, followed by 15 min of rest.

7. The method of claim 1, wherein the first threshold value for a patient having invasive ductal carcinoma is 730 and wherein the second threshold value for a patient having invasive ductal carcinoma is 200.

8. A method for optimizing diagnostic and therapeutic procedures for solid tumors in a human patient by measuring metabolic markers during exercise, the method comprising the steps of:

measuring the level of at least one metabolic marker in the patient during exercise by using a lactate and glucose analyzer;

calculating disease progression rates and sojourn times based on a personalized functional relationship between the at least one metabolic marker and disease progression rates and sojourn time;

exposing a diagnostic trait of the patient;

predicting at least one incident selected from the group consisting of: timing of screening procedures, a type of treatment, a dosage of treatment, a timing of treatment, a frequency of treatment, wherein the step of predicting is done with an algorithm that calculates a patient's metabolic score from the at least one metabolic marker; then calculates the potential personalized progression rate and sojourn time from the patient's metabolic score; then uses the calculated progression rate and sojourn time to calculate the personalized timing and frequency of screening or diagnostics procedures, or then uses the calculated progression rate and sojourn time to calculate the personalized dosage, timing and frequency of treatment, or the personalized dosage, timing and frequency of a therapeutic procedure, wherein an algorithm is used to calculate the optimal frequency of a diagnostic procedure or the optimal dosage and frequency of a therapeutic procedure from the progression rate and sojourn time; and optimizing a treatment schedule relative to an average treatment schedule, wherein the treatment schedule is extended relative to the average treatment schedule when the sojourn time exceeds a first threshold value, wherein the treatment schedule is adjusted relative to the average treatment schedule when the sojourn time is between a second threshold value and the first threshold value.

\* \* \* \* \*